United States Patent [19]

Maffrand

[11] 4,147,787
[45] Apr. 3, 1979

[54] 4,5,6,7-TETRAHYDRO-THIENO[2,3-c]-AND [3,2-c]-PYRIDINES, AND THERAPEUTIC COMPOSITIONS CONTAINING THE SAME

[75] Inventor: Jean-Pierre Maffrand, Toulouse, France

[73] Assignee: Parcor, Paris, France

[21] Appl. No.: 864,939

[22] Filed: Dec. 27, 1977

[30] Foreign Application Priority Data

Jan. 7, 1977 [FR] France .................. 77 00408

[51] Int. Cl.$^2$ .................. A61K 31/44; C07D 495/04
[52] U.S. Cl. .................. 424/256; 260/332.2 A; 546/114
[58] Field of Search .................. 260/294.8 C; 424/256

[56] References Cited

U.S. PATENT DOCUMENTS

| 3,823,151 | 7/1974 | Eichenberger et al. | 260/294.8 C |
| 3,997,545 | 12/1976 | Kuwada et al. | 260/294.8 C |
| 4,065,460 | 12/1977 | Heymes et al. | 260/294.8 C |

OTHER PUBLICATIONS

House, H., Modern Synthetic Reactions, 2nd Edition, W. A. Benjamin, Inc., Menlo Park, Cal., 1972, p. 656.

Primary Examiner—Natalie Trousof
Assistant Examiner—Richard A. Schwartz
Attorney, Agent, or Firm—Young & Thompson

[57] ABSTRACT

This invention relates to 4,5,6,7-tetrahydro-thieno[2,3-c]- and ]3,2-c]-pyridines having the formulae:

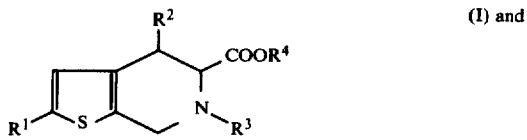

(I) and

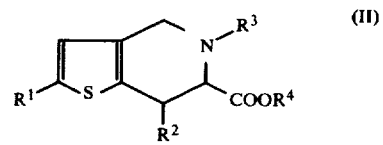

(II)

in which $R^1$ is selected from hydrogen and halogen; $R^2$ is selected from hydrogen and hydroxy; $R^3$ and $R^4$, which may be the same or different, are each selected from hydrogen, $C_{1-6}$ alkyl, phenylalkyl having 1-6 carbon atoms in the alkyl moiety, and phenyl-$C_{1-6}$alkyl substituted on the phenyl nucleus with at least a substituent selected from halogen, $C_{1-6}$ alkyl, $C_{1-6}$ alkoxy, hydroxy, nitro, cyano and trifluoromethyl; and their acid addition salts.

Said derivatives possess therapeutically useful anti-sludge, anti-thrombosis and blood-platelet aggregation inhibiting properties.

3 Claims, No Drawings

4,5,6,7-TETRAHYDRO-THIENO[2,3-c]-AND [3,2-c]-PYRIDINES, AND THERAPEUTIC COMPOSITIONS CONTAINING THE SAME

This invention relates to new 4,5,6,7-tetrahydro-thieno[2,3-c]- and [3,2-c]pyridines, and to their therapeutic applications.

The new derivatives of this invention have the following formulae:

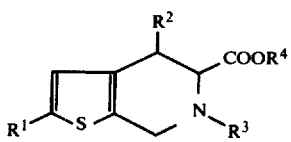

(I) and

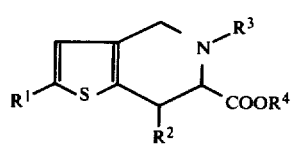

(II)

in which:
- R¹ represents hydrogen or halogen, typically chlorine;
- R² represents hydrogen or a hydroxy group;
- R³ and R⁴, which may be the same or different, represent each hydrogen or an alkyl radical having 1-6 carbon atoms or a phenylalkyl group having 1-6 carbon atoms in the alkyl moiety, optionally substituted on the phenyl nucleus with at least 1 (typically 1-3) halogen atom(s) or $C_{1-6}$ alkyl, $C_{1-6}$ alkoxy, hydroxy, nitro, cyano or trifluoromethyl group(s).

This invention includes also within its scope the inorganic or organic acid-addition salts of the derivatives of the formula (I) or (II).

Said compounds are useful for therapeutic purposes or as intermediates for synthetic procedures.

4,5,6,7-Tetrahydro-thieno-pyridine derivatives have already been disclosed in French Pat. Nos. 2,215,948 and 2,312,247; none of said references, however, discloses such derivatives which include a carboxylic group COOR⁴ ortho to the nitrogen atom of the pyridine ring.

A process for the preparation of compounds of the formula (I) or (II), comprises:

(a) condensing a compound of the formula:

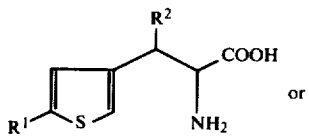

(III)

or

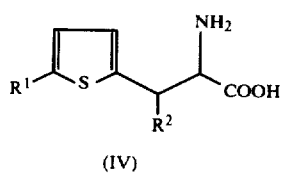

(IV)

in which R¹ and R² have the meanings given for formulae (I) and (II) with formaldehyde in aqueous solution, in the presence of a strong mineral acid, to give a derivative of the formula:

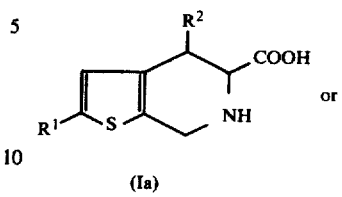

(Ia)

or

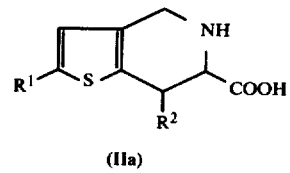

(IIa)

in which R³ = R⁴ = H;

(b) optionally reacting the derivative of the formula (Ia) or (IIa) with a halide of the formula R³X in which R³ is as defined for formulae (I) and (II), except hydrogen, and X is halogen, to give a derivative of the formula:

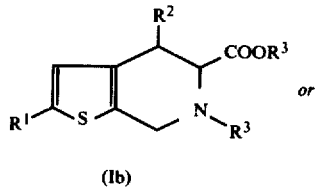

(Ib)

or

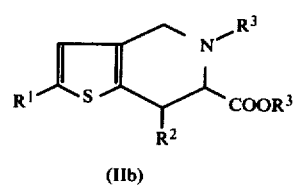

(IIb)

in which R³ = R⁴ ≠ H;

(c) optionally hydrolyzing a derivative of the formula (Ib) or (IIb), to give a derivative of the formula:

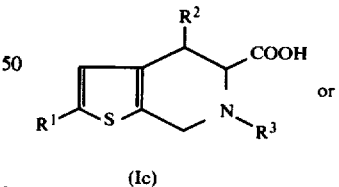

(Ic)

or

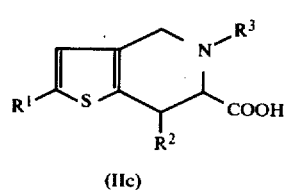

(IIc)

in which R³ ≠ H and R⁴ = H; and (d) optionally esterifying the derivatives of the formula (Ic) or (IIc) with an alcohol of the formula R⁴OH in which R⁴ is as defined for formulae (I) and (II), except hydrogen, to give a derivative of the formula:

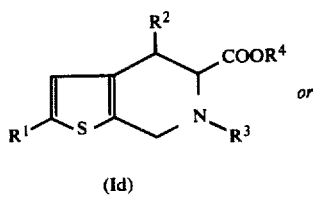

(Id)

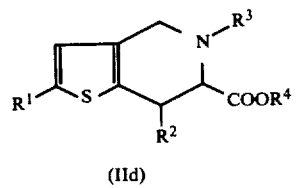

(IId)

in which $R^3 \neq R^4 \neq H$.

According to a modification, the derivatives of the formula (Ia) or (Ib) obtained in step (a) are esterified with aforesaid alcohol $R^4OH$, to give derivatives having the formula:

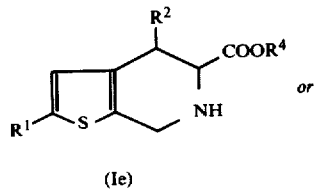

(Ie)

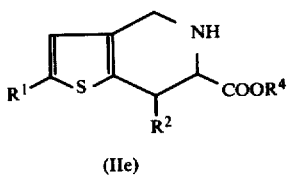

(IIe)

in which $R^3 = H$ and $R^4 \neq H$;

after which the derivative of the formula (Ie) or (IIe) is optionally reacted with the aforesaid halide of the formula $R^3X$, to give the derivatives of the formula (Id) or (IId).

The reaction of step (a), in which the inorganic acid is typically hydrochloric acid or sulfuric acid, occurs generally at room temperature; in some cases, however, it may be necessary to warm the reaction mixture, to a temperature of 50° C., for example.

In step (b), the derivatives (Ia) and (IIa) are reacted with halide $R^3X$, preferably in a slight excess, X being preferably chlorine, bromine or iodine. The reaction is advantageously conducted within an inert solvent such as a lower alcohol, for example ethanol, or dimethylformamide, in the presence of an acid binding agent such as an alkali metal carbonate, for example potassium carbonate; the reaction temperature is generally between 60° C. and the boiling temperature of the solvent used.

When X is chlorine or bromine, a catalytic or stoichiometric amount of an alkali metal iodide such as potassium iodide may be advantageously added.

The resulting compounds (Ib) and (IIb) may be submitted to a basic hydrolysis by refluxing in an alcohol solvent such as methanol or ethanol, in the presence of an alkali metal hydroxide such as sodium hydroxide, to give the derivatives (Ic) and (IIc).

The latter may, in turn, be esterified by refluxing in an alcohol of the formula $R^4OH$ in the presence of gaseous hydrogen chloride, to give derivatives (Id) and (IId).

According to the aforementioned modification, compounds (Ia) and (IIa) may also be esterified by refluxing in an alcohol of the formula $R^4OH$ in the presence of gaseous hydrogen chloride, to give derivatives (Ie) and (IIe) which, in turn, may be converted to compounds (Id) and (IId) by condensation with a halide of the formula $R^3X$, under the aforesaid conditions.

The alanines of the formula (III) or (IV) ($R^1 = H$ or Hal; $R^2 = H$) and the serines of the formula (III) or (IV) ($R^1 = H$ or Hal; $R^2 = OH$) required for the process of this invention may be obtained in the following manner:

β-(2-thienyl)alanine is a commercial product which may be prepared according to K. Dittmer, W. Herz and J. S. Chambers, J. Biol. Chem., 1946, 166,541.

β-(2-thienyl)serine may be prepared according to G. Weitnauer, Gazz. Chim. Ital., 1951, 81, 162.

β-(5-Chloro-2-thienyl)alanine may be prepared according to F. Crowe and F. F. Nord, J. Org. Chem., 1950, 15, 688.

β-(5-chloro-2-thienyl)serine may be prepared from 5-chloro-2-thienaldehyde, by adapting the aforesaid process according to G. Weitnauer: white crystals, M.p. (dec.) = 200°–205° C., Yield: 83%.

β-(3-thienyl)-alanine may be prepared according to J. Shapira, R. Shapira and K. Dittmer, J. Am. Chem. Soc., 1953, 75, 3655.

β-(3-thienyl)serine may be prepared from 3-thienaldehyde, by adapting the aforesaid process according to G. Weitnauer. Hydrochloride: white crystals, M.p. = 241° C.

The other derivatives of the formulae (III) and (IV) may be prepared according to one of the aforesaid methods.

All the serines used possessed the threo configuration and, consequently, the thienopyridines of the formula (I) and (II) derived therefrom, in which $R^2 = OH$, exhibited the cis configuration.

The inorganic (hydrochloric, sulfuric, and the like) or organic (maleic, and the like) acid addition salts may be prepared by methods well known by those expert in the art.

The following non limiting examples are given to illustrate the preparation of compounds of this invention.

EXAMPLE 1

6-Carboxy-7-hydroxy-4,5,6,7-tetrahydro-thieno[3,2-c]pyridine (Formula IIa; $R^1 = H$; $R^2 = OH$; $R^3 = R^4 = H$)

A solution of 205 g (1 mole) β-(2-thienyl)serine in 1200 cc of a 35% aqueous formalin solution and 1100 cc 0.5N sulfuric acid is stirred at room temperature for 72 hours, under a nitrogen atmosphere. The resulting light beige precipitate is washed moderately with water and dried in vacuo: M.p. > 260° C. (102.5 g). The amount of aqueous sodium hydroxide solution required to neutralize exactly all the sulfuric acid used in the reaction is added to the filtrate. The resulting new precipitate is filtered, washed with a small amount of water, and then with ethanol and with ether to give, after drying in vacuo, a second crop (43.5 g) of the desired product. Overally yield: 73%.

EXAMPLE 2

6-Carboxy-4,5,6,7-tetrahydro-thieno[3,2-c]pyridine (Formula IIa; $R^1 = R^2 = R^3 = R^4 = H$)

Obtained according to the procedure of Example 1, from β-(2-thienyl)alanine. White crystals: M.p. > 260° C. ($H_2O$); Yield: 76%.

EXAMPLE 3

6-Carboxy-2-chloro-7-hydroxy-4,5,6,7-tetrahydro-thieno[3,2-c]pyridine (Formula IIa; $R^1$ = Cl; $R^2$ = OH; $R^3 = R^4 = H$)

Obtained according to the procedure of Example 1, from β-(5-chloro-2-thienyl)serine. White crystals: M.p. > 260° C.; Yield: 43%.

EXAMPLE 4

6-Carboxy-2-chloro-4,5,6,7-tetrahydro-thieno[3,2-c]pyridine (Formula IIa; $R^1$ = Cl; $R^2 = R^3 = R^4 = H$)

Obtained according to the procedure of Example 1, from β-(5-chloro-2-thienyl)alanine. White crystals: M.p. > 260° C.; Yield: 75%.

EXAMPLE 5

5-Carboxy-4-hydroxy-4,5,6,7-tetrahydro-thieno[2,3-c]pyridine (Formula Ia; $R^1$ = H; $R^2$ = OH; $R^3 = R^4 = H$)

Obtained according to the procedure of Example 1, from β-(3-thienyl)serine. White crystals; M.p. > 260° C.; Yield: 75%.

EXAMPLE 6

5-Carboxy-4,5,6,7-tetrahydro-thieno[2,3-c]pyridine (Formula Ia; $R^1 = R^2 = R^3 = R^4 = H$)

Obtained according to the procedure of Example 1, from β-(3-thienyl)alanine. Hydrochloride: white crystals; M.p. > 260° C.; Yield: 87%.

EXAMPLE 7

5-Benzyl-6-benzyloxycarbonyl-7-hydroxy-4,5,6,7-tetrahydro-thieno[3,2-c]pyridine (Formula IIb; $R^1$ = H; $R^2$ = OH; $R^3 = R^4$ = benzyl)

A mixture of 20.5 g (0.103 mole) 6-carboxy-7-hydroxy-4,5,6,7-tetrahydro-thieno[3,2-c]pyridine from Example 1, 28.4 g (0.206 mole) potassium carbonate and 200 mg potassium iodide in 150 cc dimethylformamide is heated at 80° C. for 30 minutes. Benzyl chloride (26.07 g; 0.206 mole) is then added and the reaction mixture is stirred at 100° C. for 4 hours. After cooling, the inorganic salts are filtered off, the filtrate is evaporated to dryness and the residue is dissolved in ether. The organic phase is washed with water, dried over sodium sulfate and evaporated to dryness. The resulting oil is converted to the hydrochloride which is recrystallized twice from ethanol: white crystals: M.p. = 175°-185° C. Yield: 52%.

EXAMPLE 8

5-o-Chlorobenzyl-6-o-chlorobenzyloxycarbonyl-7-hydroxy-4,5,6,7-tetrahydro-thieno[3,2-c]pyridine (Formula IIb; $R^1$ = H; $R^2$ = OH; $R^3 = R^4$ = o-chlorobenzyl)

Obtained according to a procedure analogous to that of Example 7. Hydrochloride: white crystals: M.p. = 160°-180° C. (isopropanol); Yield: 48.5%.

EXAMPLE 9

5-o-Methylbenzyl-6-o-methylbenzyloxycarbonyl-7-hydroxy-4,5,6,7-tetrahydro-thieno[3,2-c]pyridine (Formula IIb; $R^1$ = H; $R^2$ = OH; $R^3 = R^4$ = o-methylbenzyl)

Obtained according to a procedure analogous to that of Example 7. Hydrochloride: white crystals: M.p. 180°-190° C. (isopropanol-ethanol); Yield: 48%.

EXAMPLE 10

4-Hydroxy-5-o-fluorobenzyloxycarbonyl-6-o-fluorobenzyl-4,5,6,7-tetrahydro-thieno[2,3-c]pyridine (Formula Ib; $R^1$ = H; $R^2$ = OH; $R^3 = R^4$ = o-fluorobenzyl)

Obtained according to a procedure analogous to that of Example 7, from 4-hydroxy-5-carboxy-4,5,6,7-tetrahydro-thieno[2,3-c]pyridine (Example 5) and o-fluorobenzyl chloride. Hydrochloride: pale yellow crystals, M.p. = 175° C. (ethanol); Yield: 57%.

EXAMPLE 11

4-Hydroxy-5-benzyloxycarbonyl-6-benzyl-4,5,6,7-tetrahydro-thieno[2,3-c]pyridine (Formula Ib; $R^1$ = H; $R^2$ = OH; $R^3 = R^4$ = benzyl)

Obtained according to a procedure analogous to that of Example 10. Hydrochloride: white crystals, M.p. = 160°-165° C. (ethanol-diisopropyl ether); Yield: 47%.

EXAMPLE 12

5-Benzyl-6-benzyloxycarbonyl-4,5,6,7-tetrahydro-thieno[3,2-c]pyridine (Formula IIb; $R^1 = R^2$ = H; $R^3 = R^4$ = benzyl)

Obtained according to a procedure analogous to that of Example 7, from 5-carboxy-4,5,6,7-tetrahydro-thieno[3,2-c]pyridine (Example 2) and benzyl chloride. Hydrochloride: white crystals, M.p. = 135°-140° C. (isopropanol), Yield: 65%.

EXAMPLE 13

5-o-Chlorobenzyl-6-o-chlorobenzyloxycarbonyl-4,5,6,7-tetrahydro-thieno[3,2-c]pyridine (Formula IIb; $R^1 = R^2$ = H; $R^3 = R^4$ = o-chlorobenzyl)

Obtained according to a procedure analogous to that of Example 12. Hydrochloride: white crystals, M.p. 120°-130° C. (ethanol-isopropanol); Yield: 20%.

EXAMPLE 14

5-p-Methoxybenzyl-6-p-methoxybenzyloxycarbonyl-4,5,6,7-tetrahydro-thieno[3,2-c]pyridine (Formula IIb; $R^1 = R^2 = H$; $R^3 = R^4 =$ p-methoxybenzyl)

Obtained according to a procedure analogous to that of Example 12. Base: white crystals: M.p. 72° C. (isopropanol); Yield: 31%.

EXAMPLE 15

5-p-Nitrobenzyl-6-p-nitrobenzyloxycarbonyl-4,5,6,7-tetrahydro-thieno[3,2-c]pyridine (Formula IIb; $R^1 = R^2 = H$; $R^3 = R^4 =$ p.nitrobenzyl)

Obtained according to a procedure analogous to that of Example 12. Base: beige crystals; M.p. 122° C. (acetonitrile); Yield: 51.5%.

EXAMPLE 16

5-o-Cyanobenzyl-6-o-cyanobenzyloxycarbonyl-4,5,6,7-tetrahydro-thieno[3,2-c]pyridine (Formula IIb; $R^1 = R^2 = H$; $R^3 = R^4 =$ o-cyanobenzyl)

Obtained according to a procedure analogous to that of Example 12. Base: white crystals, M.p. 107° C. (isopropanol-acetonitrile); Yield: 44%.

EXAMPLE 17

5-(3,4,5-Trimethoxy-benzyl)-6-(3,4,5-trimethoxy-benzyl-oxycarbonyl)-4,5,6,7-tetrahydro-thieno[3,2-c]pyridine (Formula IIb; $R^1 = R^2 = H$; $R^3 = R^4 =$ 3,4,5-trimethoxybenzyl)

Obtained according to a procedure analogous to that of Example 12. Hydrochloride: white crystals, M.p. 150°-170° C. (ethanol); Yield: 12%.

EXAMPLE 18

5-Butyl-6-butoxycarbonyl-4,5,6,7-tetrahydro-thieno[3,2-c]pyridine (Formula IIb; $R^1 = R^2 = H$; $R^3 = R^4 =$ butyl)

Obtained according to a procedure analogous to that of Example 12. Hydrochloride: white crystals, M.p. 141° (isopropanol-diisopropyl ether); Yield: 46%.

EXAMPLE 19

5-Phenethyl-6-phenethyloxycarbonyl-4,5,6,7-tetrahydro-thieno[3,2-c]pyridine (Formula IIb; $R^1 = R^2 = H$; $R^3 = R^4 =$ phenethyl)

Obtained according to a procedure analogous to that of Example 12. Oxalate: white crystals, M.p. 160° C. (ethanol); Yield: 17%.

EXAMPLE 20

5-Benzyloxycarbonyl-6-benzyl-4,5,6,7-tetrahydro-thieno[2,3-c]pyridine (Formula Ib; $R^1 = R^2 = H$; $R^3 = R^4 =$ benzyl)

Obtained according to a procedure analogous to that of Example 7, from 5-carboxy-4,5,6,7-tetrahydro-thieno[2,3-c]pyridine (Example 6) and benzyl chloride. Hydrochloride: pale yellow crystals; M.p. 135°-140° C. (isopropanol); Yield: 53%.

EXAMPLE 21

2-Chloro-5-benzyl-6-benzyloxycarbonyl-4,5,6,7-tetrahydro-thieno[3,2-c]pyridine (Formula IIb; $R^1 = Cl$; $R^2 = H$; $R^3 = R^4 =$ benzyl)

Obtained according to a procedure analogous to that of Example 7, from 2-chloro-6-carboxy-4,5,6,7-tetrahydro-thieno[3,2-c]pyridine (Example 4) and benzyl chloride. Hydrochloride: beige crystals, M.p. 140°-160° C.; Yield: 56%.

EXAMPLE 22

5-Benzyl-6-carboxy-4,5,6,7-tetrahydro-thieno[3,2-c]pyridine (Formula IIc; $R^1 = R^2 = H$; $R^3 =$ benzyl; $R^4 = H$)

A solution of 8 g. (0.02 mole) 5-benzyl-6-benzyloxycarbonyl-4,5,6,7-tetrahydro-thieno[3,2-c]pyridine hydrochloride (Example 12) and 7 cc aqueous sodium hydroxide (d = 1.38) in 70 cc ethanol is refluxed for 2 hours. The resulting precipitate is dissolved by addition of glacial acetic acid. After evaporating to dryness, the residue is taken up into methylene chloride and water. The organic phase is washed with water, dried over sodium sulfate and evaporated to dryness. The residue is recrystallized twice from dimethylformamide: white crystals, M.p. 230° C. Yield: 69.5%.

EXAMPLE 23

5-o-Chlorobenzyl-6-carboxy-4,5,6,7-tetrahydro-thieno[3,2-c]pyridine (Formula IIc; $R^1 = R^2 = H$; $R^3 =$ o-chlorobenzyl; $R^4 = H$)

Obtained according to a procedure analogous to that of Example 22. Hydrochloride: white crystals, M.p. 175°-180° C. (ethanol), Yield: 55.5%.

EXAMPLE 24

5-(3,4,5-Trimethoxy-benzyl)-6-carboxy-4,5,6,7-tetrahydro-thieno[3,2-c]pyridine (Formula IIc; $R^1 = R^2 = H$; $R^3 =$ 3,4,5-trimethoxybenzyl; $R^4 = H$)

Obtained according to a procedure analogous to that of Example 22. Base: beige crystals, M.p. 199° C. (isopropanol-diisopropyl ether); Yield: 57%.

EXAMPLE 25

5-Methyl-6-carboxy-4,5,6,7-tetrahydro-thieno[3,2-c]pyridine (Formula IIc; $R^1 = R^2 = H$; $R^3 =$ methyl; $R^4 = H$)

Obtained according to a procedure analogous to that of Example 22. Hydrochloride: white crystals, M.p. 180°-200° C.; Yield: 79%.

EXAMPLE 26

5-Benzyl-6-carboxy-2-chloro-4,5,6,7-tetrahydro-thieno[3,2-c]pyridine (Formula IIc; $R^1 = Cl$; $R^2 = H$; $R^3 =$ benzyl; $R^4 = H$)

Obtained according to a procedure analogous to that of Example 22. Base: beige crystals, M.p. 205° C.; Yield: 45%.

EXAMPLE 27

2-Chloro-5-benzyl-6-ethoxycarbonyl-4,5,6,7-tetrahydro-thieno[3,2-c]pyridine (Formula IId; $R^1$ = Cl; $R^2$ = H; $R^3$ = benzyl; $R^4$ = ethyl)

A slight hydrogen chloride stream is bubbled through a refluxing solution of 450 mg (1.46 mole) 2-chloro-5-benzyl-6-carboxy-4,5,6,7-tetrahydro-thieno[3,2-c]pyridine (Example 26) in 5 cc absolute ethanol. After heating for 90 minutes, the resulting precipitate is dissolved by addition of water, made basic with ammonia and extracted with ether. The ether extracts are washed with water, dried over sodium sulfate and evaporated to dryness. The resulting oil is converted to the hydrochloride which is recrystallized from isopropanol.

Beige crystals, M.p. 130°–140° C.; Yield: 46%.

EXAMPLE 28

5-Methyl-6-ethoxycarbonyl-4,5,6,7-tetrahydro-thieno[3,2-c]pyridine (Formula IId; $R^1$ = H; $R^2$ = H; $R^3$ = methyl; $R^4$ = ethyl)

Obtained according to a procedure analogous to that of Example 27, from 5-methyl-6-carboxy-4,5,6,7-tetrahydro-thieno[3,2-c]pyridine (Example 25).

Base: pale yellow oil; $b.p._{1mm}$ = 105° C.; Yield: 15%.

EXAMPLE 29

2-Chloro-5-methoxycarbonyl-4,5,6,7-tetrahydro-thieno[3,2-c]pyridine (Formula IIe; $R^1$ = Cl; $R^2$ = H; $R^3$ = H; $R^4$ = methyl)

A slight hydrogen chloride stream is bubbled through a refluxing suspension of 4.5 g 2-chloro-6-carboxy-4,5,6,7-tetrahydro-thieno[3,2-c]pyridine in 50 cc methanol. After heating for one hour, a slight amount of insoluble is filtered off and the filtrate is evaporated to dryness. After recrystallization from isopropanol, the residue gives off-white crystals, M.p. (pasty) 190°–200° C.; Yield: 52%.

EXAMPLE 30

2-Chloro-5-o.chlorobenzyl-6-methoxycarbonyl-4,5,6,7-tetrahydro-thieno[3,2-c]pyridine (Formula IId; $R^1$ = Cl; $R^2$ = H; $R^3$ = o.chlorobenzyl; $R^4$ = methyl)

A mixture of 2.1 g (7.86 mmoles) 2-chloro-6-methoxycarbonyl-4,5,6,7-tetrahydro-thieno[3,2-c]pyridine hydrochloride (Example 29), 1.27 g. (7.86 mmoles) o.-chlorobenzyl chloride and 1.1 g (7.86 mmoles) potassium carbonate in 20 cc dimethylformamide is heated at 100° C. for 21 hours. After cooling, the inorganic salts are filtered off and, after washing with ethanol, the filtrate is evaporated to dryness and the residue is dissolved in ether. The organic phase is washed with water, dried over sodium sulfate and evaporated to dryness. The residual oil is converted to the hydrochloride which, on recrystallization from isopropanol-diisopropyl ether, gives white crystals, M.p. 125°–130° C.; Yield: 30%.

The results of pharmacological and toxicological tests reported below demonstrate the properties of the derivatives of this invention, particularly their low toxicity and excellent tolerance, and their inhibiting activity on blood-platelet aggregation, their anti-sludge activity and their anti-thrombosis activity.

Thus, this invention includes also within its scope a therapeutic composition having in particular an inhibiting activity on blood-platelet aggregation, an anti-sludge activity and an anti-thrombosis activity comprising, as active ingredient, a derivative of the formula (I) or (II) or a therapeutically acceptable acid addition salt thereof, together with a pharmaceutically acceptable carrier.

I. TOXICOLOGICAL INVESTIGATION

The compounds of this invention benefit from an excellent tolerance and a low toxicity. Thus, the $LD_{50}/24h/kg$ body weight, determined orally in mice by the method according to Miller and Tainter, is in excess of 350 mg for all derivatives.

According to the same method, and by the intravenous route, the $LD_{50}/24h/kg$ body weight is, for example, 118 mg for the derivative of Example 1, 235 mg for the derivative of Example 2, 180 mg for the derivative of Example 23 and 325 mg for the derivative of Example 25.

In addition, the acute, chronic, sub-chronic and delayed toxicity tests conducted in various animal species did not evidence any local or systemic reaction, any change in the regularly effected biological control tests, any anomaly in the microscopic and macroscopic examinations conducted in the animals sacrificed and autopsied on completion of the experimentation.

II. PHARMACOLOGICAL INVESTIGATION

1. Inhibiting Activity on Blood-Platelet Aggregation

A blood sample is taken from the jugular vein of Wistar rats. From this citrated blood and after centifugation, a plasma is reconstituted which contains 600,000 ± 20,000 blood-platelets per ml, which plasma is then used in all aggregation determinations.

(a) Determination of A.D.P. Induced Blood-Platelet Aggregation 0.4 ml plasma is placed in a siliconized tube provided with a magnet bar, also siliconized. The tube is introduced into an aggregometer connected to an apparatus which records optical density variations. When light transmission has attained a stable value, 0.5 ml of a solution containing 10 μM A.D.P. (adenosinediphosphate) is added to the tube.

Blood-platelet aggregation induces an increase of light transmission, followed by a decrease subsequent to the deaggregation phase.

The maximum optical density variation thus determined characterizes the extent of the aggregation.

(b) Determination of Collagen-Induced Blood-platelet aggregation

The A.D.P. solution is substituted with a collagen (bovine tendon extract) solution.

(c) Results

Different groups of 20 rats each are used, each group being orally administered 100 mg/kg of a test derivative. The more significant results obtained in both the above tests are given in following Table I which shows the percent inhibition obtained on blood-platelet aggregation, with respect to the reference group, 3 hours after said treatment.

TABLE I

| Treatment | Percent inhibition | |
|---|---|---|
| Derivative of Example n° | A.D.P. | Collagen |
| 1 | 63.8 | 95.8 |
| 4 | 63.1 | 91.3 |
| 5 | 62.3 | 90.5 |
| 8 | 61.8 | 90.4 |
| 10 | 62.2 | 92.1 |
| 11 | 60.5 | 91.6 |
| 12 | 61.6 | 90.8 |
| 13 | 64.4 | 96.1 |
| 17 | 61.2 | 92.0 |
| 20 | 60.4 | 91.5 |
| 23 | 63.9 | 95.2 |
| 25 | 61.6 | 92.4 |
| 28 | 60.8 | 90.2 |
| 29 | 62.7 | 92.7 |
| 30 | 62.4 | 93.0 |

2. Anti-Sludge Activity

Said activity was investigated in vitro and in vivo in rats.

1. In Vitro Investigation

Thrice washed rat globules are diluted to 1/250 in physiological saline. In each of 5 tubes are placed 0.6 ml of this suspension and 0.2 ml physiological saline. To each tube is then added 0-25-50-100 and 200 μg, respectively, of the test derivative contained in 0.2 ml solution. After incubation for one hour at 37° C., 0.2 ml of a solution containing 125 μg/ml protamine sulfate are added, after which the tube is then incubated again for 0.5 hour at 37° C. The globules of each tube are then examined with a Mallases cell, and the percent free globules and the percent aggregates formed by 2, 3, 4, 5 etc.. globules is then recorded. The results of this "preventive" treatment are given in Table II.

This test demonstrates the anti-sludge activity of the derivatives of this invention.

The experiment was repeated according to a "curvative" procedure; the red corpuscles were first contacted with protamine sulfate and, after incubation for 0.5 hour, 0.2 ml containing 25 μg of test derivative were added thereto, which operation is followed by another incubation for one hour at 37° C. The results obtained are reported in Table III, in which the percent agglomerates as a function of size is indicated.

One may thus conclude that the difference between the values found for the free corpuscles of the reference test and of the test effected with the derivatives of this invention is highly significant.

2. In Vivo Investigation

200–300 g Wistar rats are anesthetized with pentobarbital (2.5 mg/kg i.p.). After central laparotomy, an intestinal loop (with its mesenterium) is exteriorized and placed in a Ringer's solution at 37° C. contained in a Petri dish opened on an inverted microscope (25 × 10). Circulation is found to be normal on examination of the mesenteric arteries. On administration of 25 mg/kg protamine sulfate by direct injection in the jugular vein, a sludge is found to occur with stasis in several arteriolae.

0.2 ml of a solution containing either 1 mg/ml, or 0.1 mg/ml test derivative is then injected into the jugular vein. The controls are administered only 0.2 ml physiological saline.

TABLE II

| Size of agglomerates | Controls | derivative of Ex. 1 | | | | derivative of Ex. 13 | | | | derivative of Ex. 23 | | | | derivative of Ex. 27 | | | |
|---|---|---|---|---|---|---|---|---|---|---|---|---|---|---|---|---|---|
| | | 25 μg | 50 μg | 100 μg | 200 μg | 25 μg | 50 μg | 100 μg | 200 μg | 25 μg | 50 μg | 100 μg | 200 μg | 25 μg | 50 μg | 100 μg | 200 μg |
| 1 ≠(free R.C.) | 33 | 64 | 69 | 86 | 89 | 65 | 68 | 87 | 90 | 60 | 65 | 78 | 83 | 62 | 66 | 75 | 84 |
| 2 | 22 | 25 | 24 | 7 | 9 | 26 | 23 | 8 | 9 | 21 | 25 | 14 | 11 | 16 | 20 | 15 | 9 |
| 3 | 13 | 11 | 5 | 4 | 2 | 9 | 5 | 3 | 1 | 16 | 6 | 5 | 4 | 17 | 10 | 7 | 5 |
| 4 | 6 | 0 | 2 | 3 | 0 | 0 | 4 | 2 | 0 | 3 | 4 | 1 | 2 | 5 | 4 | 3 | 2 |
| 5 | 5 | 0 | 0 | 0 | 0 | 0 | 0 | 0 | 0 | 0 | 0 | 0 | 0 | 0 | 0 | 0 | 0 |
| 6 | 3 | 0 | 0 | 0 | 0 | 0 | 0 | 0 | 0 | 0 | 0 | 0 | 0 | 0 | 0 | 0 | 0 |
| 7 | 5 | 0 | 0 | 0 | 0 | 0 | 0 | 0 | 0 | 0 | 0 | 0 | 0 | 0 | 0 | 0 | 0 |
| 8 | 4 | 0 | 0 | 0 | 0 | 0 | 0 | 0 | 0 | 0 | 0 | 0 | 0 | 0 | 0 | 0 | 0 |
| 9 | 2 | 0 | 0 | 0 | 0 | 0 | 0 | 0 | 0 | 0 | 0 | 0 | 0 | 0 | 0 | 0 | 0 |
| 10 | 4 | 0 | 0 | 0 | 0 | 0 | 0 | 0 | 0 | 0 | 0 | 0 | 0 | 0 | 0 | 0 | 0 |
| 11 | 2 | 0 | 0 | 0 | 0 | 0 | 0 | 0 | 0 | 0 | 0 | 0 | 0 | 0 | 0 | 0 | 0 |
| 12 | 1 | 0 | 0 | 0 | 0 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 | 0 | 0 | 0 | 0 |

≠(R.C.) = red corpuscles

TABLE III

| Size of agglomerates | Controls | Derivative of Example: | | | | | | | |
|---|---|---|---|---|---|---|---|---|---|
| | | 7 | 5 | 13 | 15 | 23 | 26 | 27 | 29 |
| 1 (free | 36 | 84 | 86 | 86 | 87 | 85 | 86 | 87 | 87 |
| 2 | 22 | 12 | 11 | 9 | 11 | 10 | 12 | 10 | 9 |
| 3 | 9 | 3 | 3 | 5 | 2 | 4 | 2 | 3 | 2 |
| 4 | 6 | 1 | 0 | 0 | 0 | 1 | 0 | 0 | 1 |
| 5 | 7 | 0 | 0 | 0 | 0 | 0 | 0 | 0 | 0 |
| 6 | 9 | 0 | 0 | 0 | 0 | 0 | 0 | 0 | 0 |
| 7 | 6 | 0 | 0 | 0 | 0 | 0 | 0 | 0 | 0 |
| 8 | 3 | 0 | 0 | 0 | 0 | 0 | 0 | 0 | 0 |
| 9 | 1 | 0 | 0 | 0 | 0 | 0 | 0 | 0 | 0 |
| 10 | 1 | 0 | 0 | 0 | 0 | 0 | 0 | 0 | 0 |

Note: use was made of 25 μg of each product

The following average results observed on 10 animals were as follows:

On injection of 1 mg/ml test derivative there is noted:

a disappearance, within 4–8 minutes, of the punctiform sludge together with reappearance of a normal circulation of the parietal plasma flow and of the axial globular flow;

the punctiform sludge images are retained in the controls.

On injection of 0.1 mg/ml test derivative, there is noted:

the disappearance of the punctiform images within the same period of time; however, normal circulation is reestablished less rapidly.

the sludge is retained in the controls.

Thus, it is apparent that the derivatives of this invention possess a high anti-sludge activity, whether the tests are effected in vitro or in vivo.

3. Anti-Thrombosis Properties

The technique used is based on that disclosed by Friedman (Amer. J. Med. Sci., 253, 83, 1967). After ether anesthesia and median laparotomy of female Wistar rats weighing 200–300 g., the vena cava inferior is made bare. A 1.8 cm long sharp metal helix is introduced in the lumen of the vessel at the level of the renal fork and "screwed" toward the iliac veins. Five hours later, the animal is again anesthetized with ether. The vena cava inferior is ligated upstream and downstream of the helix, together with the collateral veins comprised between both ligations. The helix, together with the thrombus it retains, is taken out after carefully opening the vena cava throughout the length involved; it is then dried by repeated dabbing with filter paper and is weighed a first time. Immediately thereafter, the helix is freed from its thrombus in a physiological saline bath, and is then again dried and weighed. The difference in weight gives the weight of the thrombus. It was found on histological examination that these were white thrombi.

Different groups of 10 rats each are treated by gastric intubation with one of the test derivatives, 48 hours, 24 hours and 2 hours prior to the implantation of the metal helix. Samples were taken five hours after said implantation.

Identical tests were carried out with dipyridamole and acetylsalicylic acid.

The results obtained are tabulated in Table IV: it is apparent from the resulting data that dipyridamole has no activity, that acetylsalicylic acid has little activity, whereas the derivatives of this invention have a substantial anti-thrombosis effect.

TABLE IV

| Product administered | Dosage | Body Weight | Weight of thrombus |
|---|---|---|---|
| Reference | — | 248 g | 3.75 ± 0.20 |
| derivative of Ex. 1 | 200 mg/kg | 237 g | 1.95 mg ± 0.13 |
| derivative of Ex. 6 | 200 mg/kg | 245 g | 1.85 mg ± 0.12 |
| derivative of Ex. 15 | 200 mg/kg | 243 g | 1.89 mg ± 0.14 |
| derivative of Ex. 22 | 200 mg/kg | 250 g | 1.82 mg ± 0.12 |
| derivative of Ex. 24 | 200 mg/kg | 245 g | 1.88 mg ± 0.13 |
| derivative of Ex. 27 | 200 mg/kg | 242 g | 1.95 mg ± 0.14 |
| dipyridamole | 200 mg/kg | 248 g | 3.75 mg ± 0.32 |
| Acetylsalicyclic acid | 200 mg/kg | 243 g | 3.13 mg/kg ± 0.24 |

The results obtained demonstrate the good tolerance and the useful blood-platelet aggregation inhibiting, anti-sludge and anti-thrombosis properties of the compounds of this invention which make them highly useful in human and veterinary medicine.

For oral administration, the composition of this invention may be formulated as tablets, coated tablets, capsules, drops and syrups. It may also be formulated, for rectal administration, as suppositories and, for parenteral administration, as injectable solutions.

Each unit dose contains advantageously from 0.010 g to 0.300 g active ingredient, the daily dosage regimen varying within a range from 0.010 g to 0.900 g. active ingredient, depending on the age of the patient and the condition to be treated.

Non-limiting Examples of pharmaceutical formulations of the composition of this invention are given below.

| | |
|---|---|
| 1 - Tablets | |
| derivative n°1 | 0.125 g |
| excipient: standard Aerosil, corn starch, lactose, talc | |
| 2 - Coated tablets | |
| derivative n°5 | 0.100 g |
| excipient: silicic acid, potato starch, Aerosil, sugar, lactose, talc, magnesium stearate, kaolin, shellac, gum tragacanth, rosin, starch, titanium dioxide. | |
| 3 - Capsules | |
| derivatives n°10 | 0.125 g |
| excipient: talc, lactose, Aerosil | |
| 4 - Injectable ampoules | |
| derivative n°18 | 0.075 g |
| excipient: isotonic solvent, sufficient for | 3 ml |
| 5 - Suppositories | |
| derivative n°27 | 0.100 g |
| excipient: semi-synthetic triglycerides | |

The toxicological and pharmacological investigations reported above demonstrate the good tolerance of the derivatives of this invention together with their anti-sludge, anti-thrombosis and blood-platelet aggregation inhibiting properties.

Thus the composition of this invention is usefully administrable for the preventive or curative treatment of diseases which cause a pathological modification of blood-platelet aggregation, such as thrombo-embolic diseases.

Having now described my invention what I claim as new and desire to secure by Letters Patent is:

1. Compound selected from the compounds having the formulae:

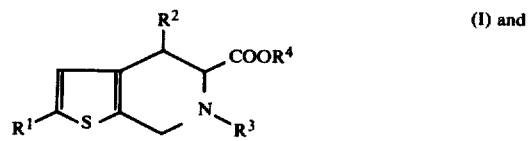
(I) and

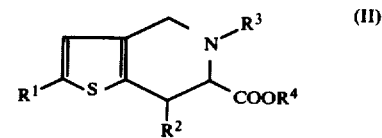
(II)

in which $R^1$ is selected from hydrogen and halogen; $R^2$ is selected from hydrogen and hydroxy; $R^3$ and $R^4$, which may be the same or different, are each selected from hydrogen, $C_{1-6}$ alkyl, phenylalkyl having 1–6 carbon atoms in the alkyl moiety, and phenyl-$C_{1-6}$ alkyl substituted on the phenyl nucleus with at least one substituent selected from halogen, $C_{1-6}$ alkyl, $C_{1-6}$ alkoxy, hydroxy, nitro, cyano and trifluoromethyl; and their therapeutically acceptable acid addition salts.

2. Therapeutic composition having an anti-sludge, anti-thrombosis and blood-platelet aggregation inhibiting activity comprising, as active ingredient, an effective anti-sludge or anri-thrombosis or blood-platelet aggregation inhibiting amount of a compound selected from the compounds having the formulae:

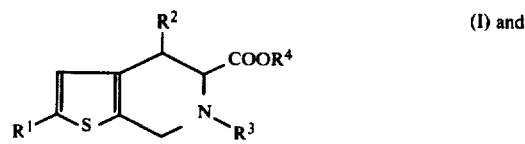
(I) and

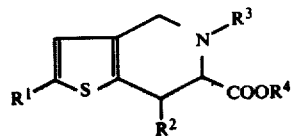

in which $R^1$ is selected from hydrogen and halogen; $R^2$ is selected from hydrogen and hydroxy; $R^3$ and $R^4$, which may be the same or different, are each selected from hydrogen, $C_{1-6}$ alkyl, phenylalkyl having 1–6 carbon atoms in the alkyl moiety, and phenyl-$C_{1-6}$ alkyl substituted on the phenyl nucleus with at least one substituent selected from halogen, $C_{1-6}$ alkyl, $C_{1-6}$ alkoxy, hydroxy, nitro, cyano and trifluoromethyl; and their therapeutically acceptable acid addition salts, together with a pharmaceutically acceptable carrier.

3. Therapeutic composition as claimed in claim 2, in unit dosage form, each unit dose containing from 0.010 g to 0.300 g active ingredient.

* * * * *